United States Patent [19]

Gaertner et al.

[11] Patent Number: 5,204,237

[45] Date of Patent: Apr. 20, 1993

[54] **UNIVERSAL AND SPECIFIC PROBES FOR *BACILLUS THURINGIENSIS* ENDOTOXIN GENES**

[75] Inventors: Frank H. Gaertner, San Diego; August J. Sick, Oceanside; George E. Schwab, La Jolla, all of Calif.

[73] Assignee: Mycogen Corporation, San Diego, Calif.

[21] Appl. No.: 737,569

[22] Filed: Jul. 26, 1991

Related U.S. Application Data

[63] Continuation of Ser. No. 427,068, Oct. 25, 1989, abandoned.

[51] Int. Cl.[5] .................. C12Q 1/68; G01N 33/566; G01N 33/48; C07H 15/12
[52] U.S. Cl. ........................ 435/6; 436/501; 436/94; 935/77; 935/78; 536/24.32
[58] Field of Search ............... 435/6, 29; 436/501, 436/94; 536/26-29; 935/77, 78

[56] References Cited

U.S. PATENT DOCUMENTS 4,771,131  9/1988  Herrnstadt et al. ............... 435/91
4,853,331  8/1989  Herrnstadt et al. ............... 435/91

OTHER PUBLICATIONS

Kronstad et al., GENE 43:29–40 (1986).

Primary Examiner—Margaret Moskowitz
Assistant Examiner—Stephanie W. Zitomer
Attorney, Agent, or Firm—Saliwanchik & Saliwanchik

[57] ABSTRACT

This invention concerns novel gene probes which can be used to identify DNA from *Bacillus thuringiensis* microbes which encode insecticidally-active protein endotoxins. The invention probes greatly facilitate the search for useful microbes hosting genes which encode insecticidally-active toxins.

36 Claims, 1 Drawing Sheet

UNIVERSAL AND SPECIFIC PROBES FOR *BACILLUS THURINGIENSIS* ENDOTOXIN GENES

This application is a continuation of application Ser. No. 07/427,068, filed Oct. 25, 1989, now abandoned.

BACKGROUND OF THE INVENTION

The soil microbe *bacillus thuringiensis* (B.t.) produces a spore and a crystalline inclusion consisting of one or more insecticidal proteins referred to as δ-endotoxins. Preparations of the spores and crystals of *B. thuringiensis* subsp. kurstaki have been used for many years as commercial insecticides for insects of the order Lepidoptera. Recently, other species of B.t., namely israelensis and san diego, have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, in press). In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner, F. H. and L. Kim [1988] TIBTECH 6:S4-S7). Thus, isolated B.t. endotoxin genes are becoming commercially valuable.

Recently, many new subspecies of B.t. have been identified, and many genes responsible for active δ-endotoxin proteins have been isolated (Hofte, H., and H. R. Whitely [1989] Microbiological Reviews 242-255). Thus, many different B.t. toxins are now known. However, to date, the method for isolating the responsible toxin genes has been a slow empirical process. That is, for a given B.t. isolate, there is currently no rapid systematic method for identifying the responsible toxin genes or for predicting the activity of a given B.t. isolate, Currently, a given B.t. isolate must first be placed through a tedious series of bioassays to determine its spectrum of insecticidal activity, and subsequently an attempt is made to isolate the genes responsible for the observed insecticidal activity, generally through the nonsystematic use of mixed or randomly selected oligomeric probes.

The subject invention eliminates much of the empirical nature of finding new B.t. insecticidal protein toxin genes. This invention places the systematic isolation of novel B.t. insecticidal toxin genes and their associated δ-endotoxins within reach of the practitioner in the insect-control art and, also, enables a rapid early identification of potentially new commercially valuable insecticidal endotoxin genes.

BRIEF SUMMARY OF THE INVENTION

The subject invention concerns (1) peptide and corresponding nucleotide sequence segments which define proteins and responsible genes broadly (universally) as B.t. endotoxins, and specifically as lepidopteran, dipteran, or coleopteran-active endotoxins, and (2) the use of such nucleotide segments as either universal, group, or gene-specific probes for the systematic identification and isolation of endotoxin genes.

Specifically, the invention concerns the following sequence segments:

i) a peptide sequence whose single letter amino acid designation is "GPGFTGGD" and whose nucleotide sequence specifies the universal nucleotide probe "GGACCAGGATTTACAGGAGGAGAT" for coleopteran, lepidopteran, and dipteran-active endotoxin genes;

ii) a peptide sequence whose single letter amino acid designation is "MIHAAD" and whose nucleotide sequence specifies the group-specific nucleotide probe "ATGATTCATGCGGCAGATA" for lepidopteran-active endotoxin genes;

iii) a peptide sequence whose single letter amino acid designation is "GDFTQGVMGWH" and whose nucleotide sequence specifies the group-specific nucleotide probe "GGTGATTTTACACAAGGGGTAATGGGGTGGCATG" for dipteran-active endotoxin genes;

iv) a peptide sequence whose single letter amino acid designation is "KSKALAELQG" and whose nucleotide sequence specifies the group-specific nucleotide probe "AAAGCTCTTGCAGAGTTACAGGG" for coleopteran-active endotoxin genes;

v) A set of peptide sequences whose single letter amino acid designations are "RIILGSGP", "SPIGKCAH", "PIHFPST", "AEELPIRGGEL", "NVMESSA", "VSASTVQTG", "HVYTNHCVDT", and "VAAEIGLG" whose nucleotide sequences specify, respectively, the gene-specific nucleotide probes "GAATTATACTTGGTTCAGGCCC", "GTCCAATCGGAAAATGTGCCC", "CCAATTCACTTCCCATCGAC", "GCTGAAGAACTTCCTATTCGTGGTGGTGAGC", "CGTTATGGAGAGCAGCGCA", "GTTAGCGCATCAACAGTCCAAACGGG", "CATGTTTATACTAACCATTGTGTGGATACG", and "CGTAGCAGCAGAAATCGGCTTGGGC" for lepidopteran-active endotoxin genes;

vi) A set of peptide sequences whose single letter amino acid designations are "GGTNMNPI", and "GYPLANDLQG" whose nucleotide sequences specify, respectively, the gene-specific nucleotide probes "GGGAGGAACAAATATGAATCCTTATC", and "CAGGCTATCCGTTAGCGAATGACTTACAAGGG" for dipteran-active endotoxin genes; and vii) A set of peptide sequences whose single letter amino acid designations are "NVGAVSW", and "YNGYLGAQ" whose nucleotide sequences specify, respectively, the gene-specific nucleotide probes "AATGTTGGCGCGGTCAGCTGGG" and "TACAATGGCTATTTAGGTGCACAG" for coleopteran-active endotoxin genes.

DETAILED DISCLOSURE OF THE INVENTION

The subject invention concerns DNA probes for identifying B.t. DNA segments which encode protein toxins which are active against various insects. A systematic approach for the use of the invention probes entails first identifying by Southern blot analysis of a gene bank of the B.t. isolate all DNA segments homologous with the universal probe. Subsequently, lepidopteran, coleopteran, and dipteran-active gene segments can be identified with a similar analysis using each of the group-specific probes. The specific nature of each of the gene segments can be probed further using the sets of specific probes for lepidopteran, coleopteran, and dipteran-active genes listed above. Thus, it is possible, without the aid of biological analysis, to know in advance the probable activity of many new B.t. isolates, and of the individual endotoxin gene products expressed by a given B.t. isolate. Such a probe analysis provides a rapid method for identifying potentially commercially valuable insecticidal endotoxin genes within the multifarious subspecies of B.t.

The nucleotide segments of the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Following are examples which illustrate procedures, including the best mode, for practicing the invention. These examples should not be construed as limiting. All percentages are by weight and all solvent mixture proportions are by volume unless otherwise noted.

EXAMPLE 1

Figure 1:
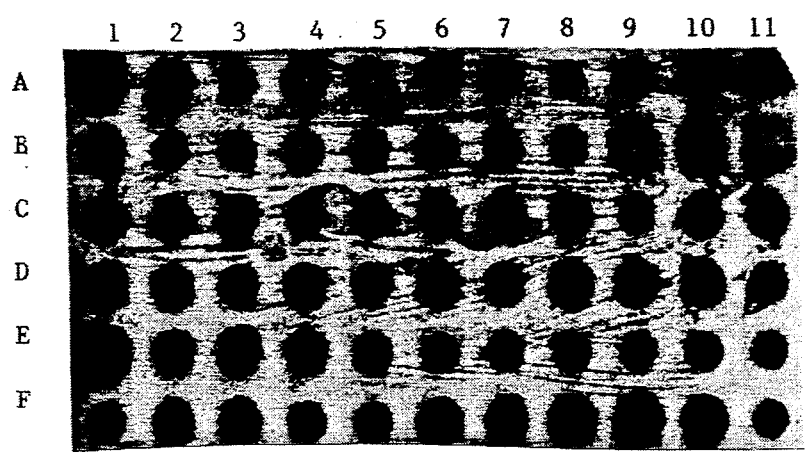
FIG. 1 shows an autoradiogram of 66 different *Bacillus thuringiensis* isolates all positively hybridizing with the "universal nucleotide probe."
Figure 2:
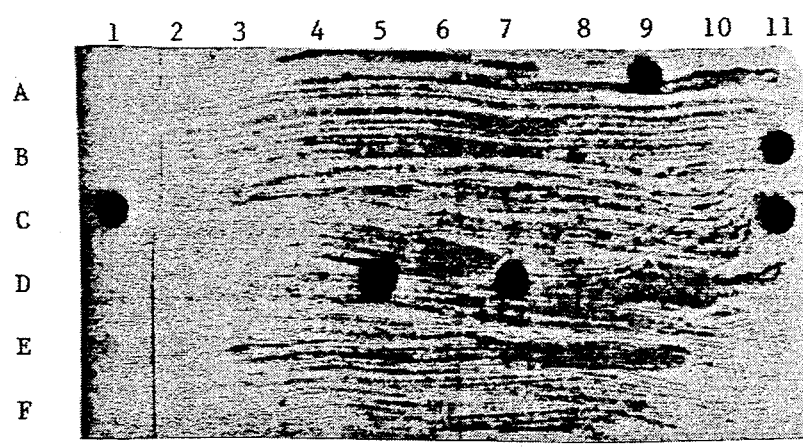
FIG. 2 shows an autoradiogram of the same 66 different *Bacillus thuringiensis* isolates as in FIG. 1, but this time probed with the "AEELPIRGGEL" gene-specific probe. Toxin genes can be identified by hybridization, i.e., A-9, B-11, C-1 and 11, and D-5 and 7 all are of the AEELPIRGGEL toxin class.

Rapid Genetic Characterization of Bacterial Soil Isolates Using Oligonucleotide Probe Hybridization to Colony (Dot) Blots The dot blot method for characterizing toxin genes in *Bacillus thuringiensis* or any bacterial soil isolate was developed because of the evaluation of an oligonucleotide probe library, the subject invention. The procedure involves growing liquid bacterial culture from a sporulated colony and filtering it through a nylon membrane on a dot blot apparatus to collect the cells. The cells are protoplasted by exposing the membrane to 3 mm paper soaked in a solution containing 30 mM lysozyme to a final pH of 8.0 for 20 minutes. This treatment is followed by a 10 minute treatment with 10% SDS, 5 minutes with 0.5N NaOH, 1.5M NaCl, 5 minutes with 1M Tris-Cl, 1.5M Nacl, pH=8.0, and 5 minutes with 2X SSPE (300 mM NaCl, 20 mM NaH$_2$OPO$_4$, 2 mM EDTA, pH =7.4). The membrane is baked in an oven for 2 hours at 80° C. The DNA of each isolate can then be characterized by hybridization with [$^{32}P$]-radiolabeled oligonucleotide probes from the library using standard hybridization and autoradiography techniques. FIGS. 1-2 given an example of the typical results displaying the use of general and specific oligonucleotide probes for genetically characterizing bacterial soil isolates.

We claim:

1. A gene probe for identifying *Bacillus thuringiensis* DNA encoding insecticidally-active protein endotoxins consisting essentially of a nucleotide sequence selected from the group consisting of
   (a) GGACCAGGATTTACAGGAGGAGAT;
   (b) ATGATTCATGCGGCAGATA;
   (c) GGTGATTTTACACAAGGG-GTAATGGGGTGGCATG;
   (d) AAAGCTCTTGCAGAGTTACAGGG;
   (e) GAATTATACTTGGTTCAGGCCC;
   (f) GTCCAATCGGAAAATGTGCCC;
   (g) CCAATTCACTTCCCATCGAC;
   (h) GCTGAAGAACTTCCTATTCGTGGTGGT-GAGC;
   (i) CGTTATGGAGAGCAGCGCA;
   (j) GTTAGCGCATCAACAGTCCAAACGGG;
   (k) CATGTTTATACTAACCATTGTGT-GGATACG;
   (l) CGTAGCAGCAGAAATCGGCTTGGGC;
   (m) GGGAGGAACAAATATGAATCCTTATC;
   (n) CAGGCTATCCGTTAGCGAATGACT-TACAAGGG;
   (o) AATGTTGGCGCGGTCAGCTGGG; and
   (p) TACAATGGCTATTTAGGTGCACAG.

2. The gene probe, according to claim 1, consisting essentially of the following sequence: GGACCAGGATTTACAGGAGGAGAT.

3. The gene probe, according to claim 1, consisting essentially of the following sequence: ATGATTCATGCGGCAGATA.

4. The gene probe, according to claim 1, consisting essentially of the following sequence: GGTGATTTTACACAAGGGGTAATGGGGTGGCATG.

5. The gene probe, according to claim 1, consisting essentially of the following sequence: AAAGCTCTTGCAGAGTTACAGGG.

6. The gene probe, according to claim 1, consisting essentially of the following sequence: GAATTATACTTGGTTCAGGCCC.

7. The gene probe, according to claim 1, consisting essentially of the following sequence: GTCCAATCGGAAAATGTGCCC.

8. The gene probe, according to claim 1, consisting essentially of the following sequence: CCAATTCACTTCCCATCGAC.

9. The gene probe, according to claim 1, consisting essentially of the following sequence: GCTGAAGAACTTCCTATTCGTGGTGGTGAGC.

10. The gene probe, according to claim 1, consisting essentially of the following sequence: CGTTATGGAGAGCAGCGCA.

11. The gene probe, according to claim 1, consisting essentially of the following sequence: GTTAGCGCATCAACAGTCCAAACGGG.

12. The gene probe, according to claim 1, consisting essentially of the following sequence: CATGTTTATACTAACCATTGTGTGGATACG.

13. The gene probe, according to claim 1, consisting essentially of the following sequence: CGTAGCAGCAGAAATCGGCTTGGGC.

14. The gene probe, according to claim 1, consisting essentially of the following sequence: GGGAGGAACAAATATGAATCCTTATC.

15. The gene probe, according to claim 1, consisting essentially of the following sequence: CAGGCTATCCGTTAGCGAATGACTTACAAGGG.

16. The gene probe, according to claim 1, consisting essentially of the following sequence: AATGTTGGCGCGGTCAGCTGGG.

17. The gene probe, according to claim 1, consisting essentially of the following sequence: TACAATGGCTATTTAGGTGCACAG.

18. A process for detecting the presence of genes, or fragments thereof, encoding a protein endotoxin active against insects selected from the group consisting of coleopteran, dipteran, and lepidopteran insects which comprises:
(a) contacting *Bacillus thuringiensis* DNA with restriction endonucleases to obtain DNA fragments;
(b) probing said DNA fragments under hybridizing conditions with a detectably labeled gene probe comprising DNA having the following sequence: GGACCAGGATTTACAGGAGGAGAT; and
(c) detecting probe DNA which has hybridized to said *Bacillus thuringiensis* DNA fragments.

19. A process for detecting the presence of genes, or fragments thereof, encoding a protein endotoxin active against insects of the order lepidoptera, which comprises:
(a) contacting *Bacillus thuringiensis* DNA with restriction endonucleases to obtain DNA fragments;
(b) probing said DNA fragments under hybridizing conditions with a detectably labeled gene probe comprising DNA having a nucleotide sequence selected from the group consisting of:
ATGATTCATGCGGCAGATA,
GAATTATACTTGGTTCAGGCCC,
GTCCAATCGGAAAATGTGCCC,
CCAATTCACTTCCCATCGAC,
GCTGAAGAACTTCCTATTCGTGGTGGTGAGC,
CGTTATGGAGAGCAGCGCA,
GTTAGCGCATCAACAGTCCAAACGGG,
CATGTTTATACTAACCATTGTGTGGATACG, and
CGTAGCAGCAGAAATCGGCTTGGGC; and
(c) detecting probe DNA which has hybridized to said *Bacillus thuringiensis* DNA fragments.

20. The process, according to claim 19, wherein said nucleotide sequence is ATGATTCATGCGGCAGATA.

21. The process, according to claim 19, wherein said nucleotide sequence is GAATTATACTTGGTTCAGGCCC.

22. The process, according to claim 19, wherein said nucleotide sequence is GTCCAATCGGAAAATGTGCCC.

23. The process, according to claim 19, wherein said nucleotide sequence is CCAATTCACTTCCCATCGAC.

24. The process, according to claim 19, wherein said nucleotide sequence is GCTGAAGAACTTCCTATTCGTGGTGGTGAGC.

25. The process, according to claim 19, wherein said nucleotide sequence is CGTTATGGAGAGCAGCGCA.

26. The process, according to claim 19, wherein said nucleotide sequence is GTTAGCGCATCAACAGTCCAAACGGG.

27. The process, according to claim 19, wherein said nucleotide sequence is CATGTTTATACTAACCATTGTGTGGATACG.

28. The process, according to claim 19, wherein said nucleotide sequence is CGTAGCAGCAGAAATCGGCTTGGGC.

29. A process for detecting the presence of genes, or fragments thereof, encoding a protein endotoxin active against insects of the order diptera, which comprises:
(a) contacting *Bacillus thuringiensis* DNA with restriction endonucleases to obtain DNA fragments;
(b) probing said DNA fragments under hybridizing conditions with a gene probe comprising DNA having a nucleotide sequence selected from the group consisting of:
GGTGATTTTACACAAGGGGTAATGGGGTGGCATG,
GGGAGGAACAAATATGAATCCTTATC, and
CAGGCTATCCGTTAGCGAATGACTTACAAGGG; and
(c) detecting probe DNA which has hybridized to said *Bacillus thuringiensis* DNA fragments.

30. The process, according to claim 29, wherein said nucleotide sequence is GGTGATTTTACACAAGGGGTAATGGGGTGGCATG.

31. The process, according to claim 29, wherein said nucleotide sequence is GGGAGGAACAAATATGAATCCTTATC.

32. The process, according to claim 29, wherein said nucleotide sequence is CAGGCTATCCGTTAGCGAATGACTTACAAGGG.

33. A process for detecting the presence of genes, or fragments thereof, encoding a protein endotoxin active against insects of the order coleoptera, which comprises:
(a) contacting *Bacillus thuringiensis* DNA with restriction endonucleases to obtain DNA fragments;
(b) probing said DNA fragments under hybridizing conditions with a gene probe comprising DNA having a nucleotide sequence selected from the group consisting of:
AAAGCTCTTGCAGAGTTACAGGG,
AATGTTGGCGCGGTCAGCTGGG, and
TACAATGGCTATTTAGGTGCACAG; and
(c) detecting probe DNA which has hybridized to said *Bacillus thuringiensis* DNA fragments.

34. The process, according to claim 33, wherein said nucleotide sequence is AAAGCTCTTGCAGAGTTACAGGG.

35. The process, according to claim 33, wherein said nucleotide sequence is AATGTTGGCGCGGTCAGCTGGG.

36. The process, according to claim 33, wherein said nucleotide sequence is TACAATGGCTATTTAGGTGCACAG.

* * * * *

UNITED STATES PATENT AND TRADEMARK OFFICE
CERTIFICATE OF CORRECTION

PATENT NO. : 5,204,237
DATED : April 20, 1993
INVENTOR(S) : Frank H. Gaertner, August J. Sick and George E. Schwab It is certified that error appears in the above-indentified patent and that said Letters Patent is hereby corrected as shown below:

Column 1   line 42: Delete "B.t. isolate," and insert --*B.t.* isolate.--.
Column 3   line 47: Delete "evaluation" and insert --evolution--.
Column 3   line 64: Delete "given" and insert --give--.

Signed and Sealed this

Twelfth Day of April, 1994

Attest:

BRUCE LEHMAN

*Attesting Officer*   *Commissioner of Patents and Trademarks*